US008529482B2

(12) United States Patent
Giontella

(10) Patent No.: US 8,529,482 B2
(45) Date of Patent: Sep. 10, 2013

(54) ORTHOPEDIC TUTOR FOR SPINE AND METHOD

(76) Inventor: Massimo Giontella, Florence (IT)

( * ) Notice: Subject to any disclaimer, the term of this patent is extended or adjusted under 35 U.S.C. 154(b) by 303 days.

(21) Appl. No.: 12/867,003

(22) PCT Filed: Feb. 10, 2009

(86) PCT No.: PCT/IT2009/000050
§ 371 (c)(1),
(2), (4) Date: Aug. 10, 2010

(87) PCT Pub. No.: WO2009/101650
PCT Pub. Date: Aug. 20, 2009

(65) Prior Publication Data
US 2011/0004136 A1 Jan. 6, 2011

(30) Foreign Application Priority Data
Feb. 14, 2008 (IT) .................. FI2008A0024

(51) Int. Cl.
*A61F 5/00* (2006.01)
(52) U.S. Cl.
USPC .......................................... 602/18
(58) Field of Classification Search
USPC ............... 602/17, 18, 19, 5, 6, 12, 32, 36, 38, 602/40; 128/846, 869, 97.1, DIG. 23
See application file for complete search history.

(56) References Cited

U.S. PATENT DOCUMENTS

| | | | | | |
|---|---|---|---|---|---|
| 2,223,276 A | * | 11/1940 | Ward | ............................... | 602/18 |
| 2,735,424 A | * | 2/1956 | Benjamin | ...................... | 602/17 |
| 2,904,040 A | * | 9/1959 | Hale | ............................... | 602/18 |
| 3,548,817 A | * | 12/1970 | Mittasch | ......................... | 602/36 |
| 3,771,513 A | * | 11/1973 | Velazquez | ....................... | 602/19 |
| 3,776,224 A | * | 12/1973 | McFarland | ...................... | 602/18 |
| 3,945,376 A | * | 3/1976 | Kuehnegger | ................... | 602/19 |
| 4,628,913 A | * | 12/1986 | Lerman | ........................... | 602/18 |
| 6,206,846 B1 | * | 3/2001 | Kenney | ............................ | 602/17 |
| 6,267,741 B1 | * | 7/2001 | Lerman | ........................... | 602/18 |
| 6,503,213 B2 | * | 1/2003 | Bonutti | ............................. | 602/5 |
| 6,770,047 B2 | * | 8/2004 | Bonutti | ........................... | 602/18 |

* cited by examiner

*Primary Examiner* — Patricia Bianco
*Assistant Examiner* — Raymond E Harris
(74) *Attorney, Agent, or Firm* — Pearne & Gordon LLP

(57) ABSTRACT

The tutor of this invention is made up of a support (1) to be fixed to the chest of the user with a chin rest (2) being connected to the support (1) through a hinge (7) and also being anchored at an element (3) provided on the patient's neck, and of a plate (4) positioned on the convexity of the patient's dorsal curve and having applied thereto a posteroanterior thrust. The said chin rest (2) is engaged to a means (8) articulated to the support element (1) in a central position with respect to the chin rest (2) and is able to generate and adjust an anteroposterior upwardly oblique thrust F on the chin of the user. The method for using the said tutor implies putting on and fitting the chin rest, then manually activating the means (8) engaged on the chin rest (1) so as to obtain, on the chin of the user, who keeps his/her mouth shut and head reclined forward, a desired anteroposterior upwardly oblique thrust F which, via the user's yaw, transmits to the atlas bone (first vertebra of rachis) an equal force R whose horizontal component Ro is cause for a retropositioning of the cervical curve, and whose vertical component Rw is cause for an upwardly directed stretching and, consequently, a direct straightening of the underlying dorsal curve.

13 Claims, 6 Drawing Sheets

ORTHOPEDIC TUTOR FOR SPINE AND METHOD

FIELD OF THE INVENTION

The invention refers to orthopedic apparatuses. In particular, the object of the invention is an orthopedic tutor for bloodless correction of vertebral deformities and the method for the use thereof.

An induced active self-correction is proposed which is operated by a retropositioning of the cervical curve and by a concurrent upward stretching thereof that are obtained by applying, on the patient's chin, an upward oblique anteroposterior thrust F which, by means of the yaw, is transmitted to the Atlas bone (first vertebra of the rachis) with an anteroposterior horizontal component $F_O$ and a vertical component $F_V$ (FIG. 1). The correction of the cervical curve thus obtained causes the intervention of the paravertebral and intercostal muscles the involvement of which generates also the general stabilization of the rachis.

DESCRIPTION OF RELATED ART

As everybody knows, the backbone consists of seven cervical vertebrae for sustaining the neck and head, of twelve dorsal vertebrae for sustaining the chest, of five lumbar vertebrae for sustaining the abdomen and of two bones which close the pelvis cavity (sacrum and coccyx).

The backbone, when viewing it in the front plane, is rectilinear, whereas in the sagittal plane exhibits four anteroposterior curves, two of which having anterior convexity (cervical lordosis and lumbar lordisis) and two having posterior convexity (dorsal kyphosis and sacral kyphosis).

The vertebrae of the cervical, dorsal and lumbar regions are articulated to each other to make it possible, with their elongation and compression, to absorb the variable stresses by preserving the integrity of the articular structures and favoring the kinematic capacity of the whole vertebral complex and of the structures correlated therewith.

However, all the vertebral curves have a range within which they must remain able to exert their function correctly. When the degree of curvature increases excessively, the curves become a negative factor for the stability and functionality of the rachis, inasmuch as they loose their shock-absorbing capacity.

The pathologic increases of the physiologic vertebral curves are called hyperlordosis and hyperkyphosis, which are very serious pathological pictures involving also alterations of the functionality of the paravertebral muscles.

The most common pathological picture of vertebral curves is the dorsal hyperkyphosis, that is, a dorsal curve exceeding 35°. Such an alteration may occur both in the childhood, owing to vertebral osteochonondrosis (suffering of growth nuclei of the vertebral bodies), and in the senile age, owing to osteoporosis which determines the compression of the vertebral bodies, and to vertebral arthrosis.

At present, the bloodless treatment of the dorsal hyperkyphosis is obtained with various orthopedic systems.

A first system consists in exerting a pressure in horizontal direction onto the dorsal convexity and, at the same time, a horizontal counter-pressure onto the sternum and abdomen, respectively. This system is implemented by using a waistcoat commonly called ("of three points of action type"); however, this system exhibits the drawback that the counter-pressure exerted onto the abdomen has a limited effect inasmusch as the members held therein reduce significantly the thrust thereon in the lower region of the dorsal curve.

A further system consists in exploiting the continuity of the dorsal spine with the lumbar spine and in causing a passive pressure onto the dorsal curve, following a reduction of the lumbar lordosis, obtained by a horizontal pelvic anteroposterior thrust and a horizontal counter-thrust onto the convexity of the dorsal curve and a stimulus provided by the cervical collar for a self-correction which results practically ineffectual. This system is implemented by the Milwaukee corrective waistcoat, and is suited exclusively for teenagers with a growing neck, while it is inapplicable and ineffectual in adults and elderly people. Moreover, the passive pressure onto the dorsal curve determines the hypotonicity of paravertebral and intercostal muscles so that, in many cases, upon the removal of the corrector, there is occur often the reapperance of the hyperkyphosis and instability of rachis.

Yet another system consists in exerting an upwardly directed pull of the whole backbone. This is obtained with a HALO type apparatus by which a plurality of pull points are fixed on the skullcap and a downwardly directed thrust is exerted onto the pelvis.

In the state-of-the art, none of the known system provides for the correction of the dorsal hyperkyphosis by acting directly on the cervical curve from above and involving the paravertebral and intercostal muscles.

SUMMARY AND DETAILED DESCRIPTION OF THE INVENTION

Reduced to its essential construction, said orthopedic tutor comprises:
- a support element (1) with its front part intended to remain adherent to the patient's chest, with the upper part being provided with two stretched apart and symmetrical edges (11), centrally joined to a chin rest (2) able to oscillate vertically for accomodating the patient's chin, and to be anchored laterally to an element (3) provided on the patient's necks close to the nape;
- a plate (4) of rigid material to be positioned in correspondence of the convexity of the patient's dorsal curve and supported in position by two belts (5) passing on the patient's shoulders and apt to be anchored to the upper part of the support element (1): the intensity of the posteroanterior thrust Fp to be exerted onto said plate (4) being adjustable by means of a belt (6) tightened around the patient's body and fixed to the element (1) with the interposition of a buckle (7) provided on the two sides of the lower part of support element (1).

More particularly:
- the said support element (1) is made of rigid material, with its front part (10) suitably shaped to ensure the application thereof in adhering condition to the patient's chest;
- the said chin rest (2) is made to oscillate vertically with respect to said support element (1) by means of a hinge (7a) shaped as a horizontal pivot provided in the lower part of the same chin rest and being acted upon by said thrust F (with closed mouth and forwardly reclined head of the patient) which is generated by a cam (8) which is in turn articulated to the fixed element (1) in front of the chin rest, the manual rotation of said cam (8) making it possible to adjust the intensity of thrust F.

As an alternative to said cam, use can be made either of a screw with relevant nut screw, or of a spring whose longitudinal axes shall be perpendicular to the chin rest (2).

A retainer element, of a type known per se, is provided for holding tightly the element (8) on the chin rest. The orthopedic tutor is provided with a retainer element for locking the means (8a) in order to keep constant in time the intensity of the thrust (F) generated by the said means. The tensile means (6) consist of a belt connected to the plate (4) wound up around the patient's body and fixed to the lower part of support element (1) by means of one or two buckles (7).

The method for using the orthopedic tutor according to the invention comprises:

putting on the tutor by laying the support (1) onto the user's chest and fixing it therein by belt(s) (6) anchored to the dorsal plate (4) and wrapped around the body by means of the two belts (5) also anchored to the plate (4) and passing over the shoulders;

fitting the chin rest (2) by tensioning the anchoring elastic band (3a) at the back of the nape;

activating the means (8a) intended to exert on the user's chin the desired thrust F which acts substantially in the anteroposterior direction with respect to the user and is upwardly oblique, that is, gives rise to a horizontal component $F_O$ directed toward the user and a vertical component Fv directed upwardly;

transmitting to the user's atlas bone, that is, to the first vertebra of his/her cervical curve which is connected to the skull, a force R of intensity equal to the thrust F which results as having a horizontal anteroposterior component $R_O$ equal to the component $F_O$ of thrust F and a vertical component $R_V$ upwardly directed and equal to $F_V$; said force $R_O$ on the atlas determining a repositioning of the user's cervical curve and, at the same time, the said $R_V$ determining an upwardly directed stretching of same cervical curve.

For the correction of the dorsal curve by the said method, provision is made advantageously for applying a cooperating horizontal posteroanterior thrust $F_P$ on the plate (4) placed on the convexity of the dorsal curve, through a proprioceptive stimulation of the muscle activity: this being possible by tensioning the belt(s) (6) of the tutor.

The advantages obtainable with the orthopedic tutor according to the present invention are outstanding. The major advantage lies in the involvement of the paravertebral and intercostal muscles, with the additional effect of contributing to the straightening of the cervical and lumbar lordosis, as well as of the hyperkyphosis associated with the scoliosis (deviation of the backbone on the frontal plane).

A further advantage is that it can be applied to adults and elderly people and in most serious cases where there is a forward drop of the rachis due to the reversal of the cervical lordosis, as well as in serious forms of cervical arthrosis and slipped cervical disc, owing to the decompression effect onto the nervous structures.

Further advantages lie in the possibility of using a tutor of simple and cost-effective manufacturing, of easy application, allowing a handy adjustment of the thrust onto the chin by the same patient, and of such good tolerability and functionality as to be wearable also for a few hours per day; it allows reducing the necessary application thereof to a partial period of the day. Besides, the correction of the cervical curve thus obtained determines the crucial intervention of the paravertebral and intercostal muscles whose involvement generates and ensures also the general stabilization of the rachis. The method of the invention determines a reflex action of the paravertebral and intercostal muscles which contributes to the correction of the various vertebral segments which make up the rachis.

F is the upwardly oblique and anteroposterior thrust to be applied on the user's chin;

$F_O$ is the horizontal anteroposterior component;

$F_V$ is the upward vertical component;

$F_1 = F_2 = \frac{1}{2} F$ are two equal parallel forces passing through the points T1 and T2 of attachment of the yaw to the skull;

R is the resultant of said two forces $F_1$, $F_2$ which is transmitted to the atlas bone and has intensity equal to F, with the anteroposterior component $R_O$ and upward vertical component $R_V$.

Figure 2:
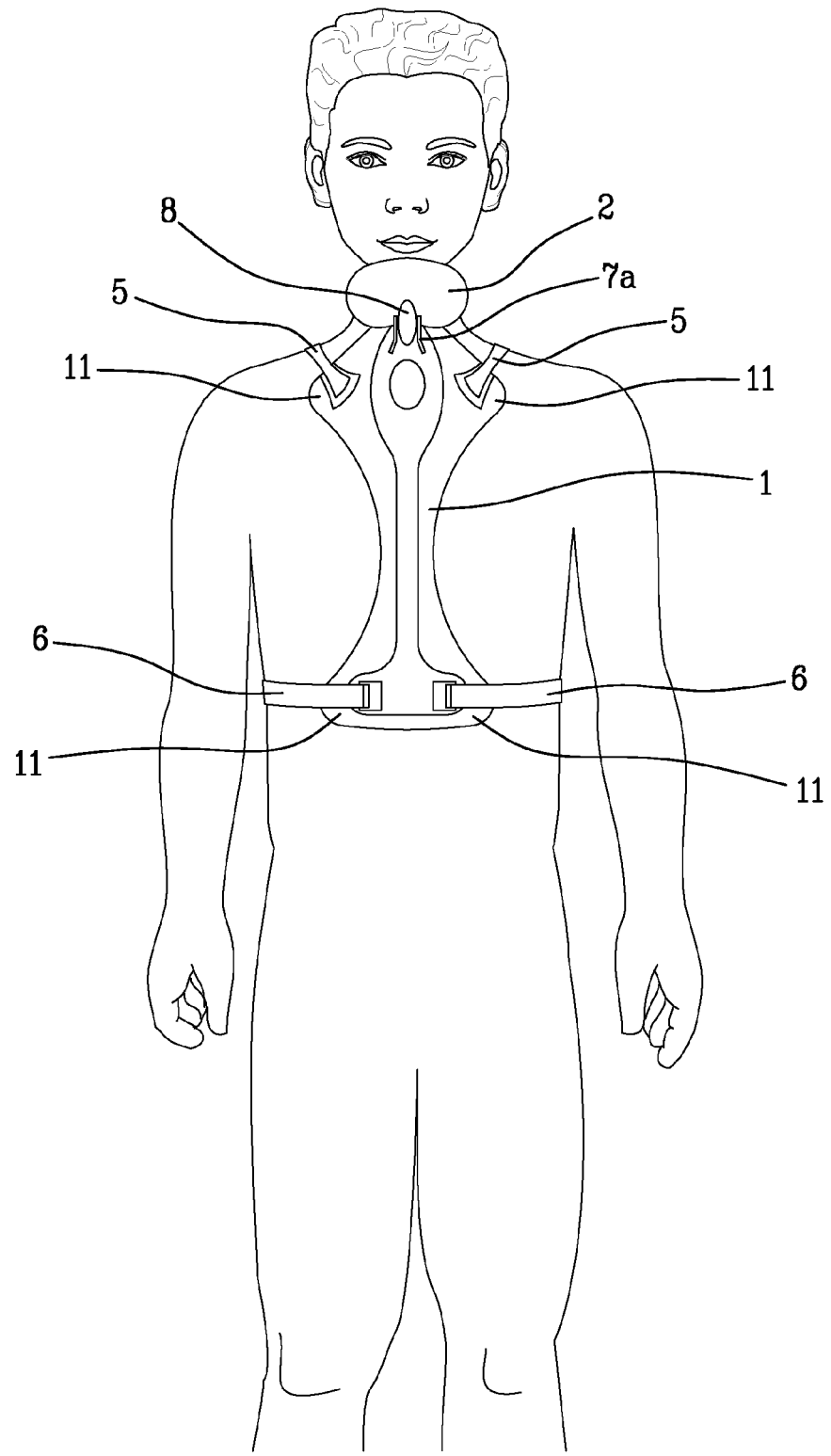

FIG. 2 is a front view of the tutor in use.

Figure 1:
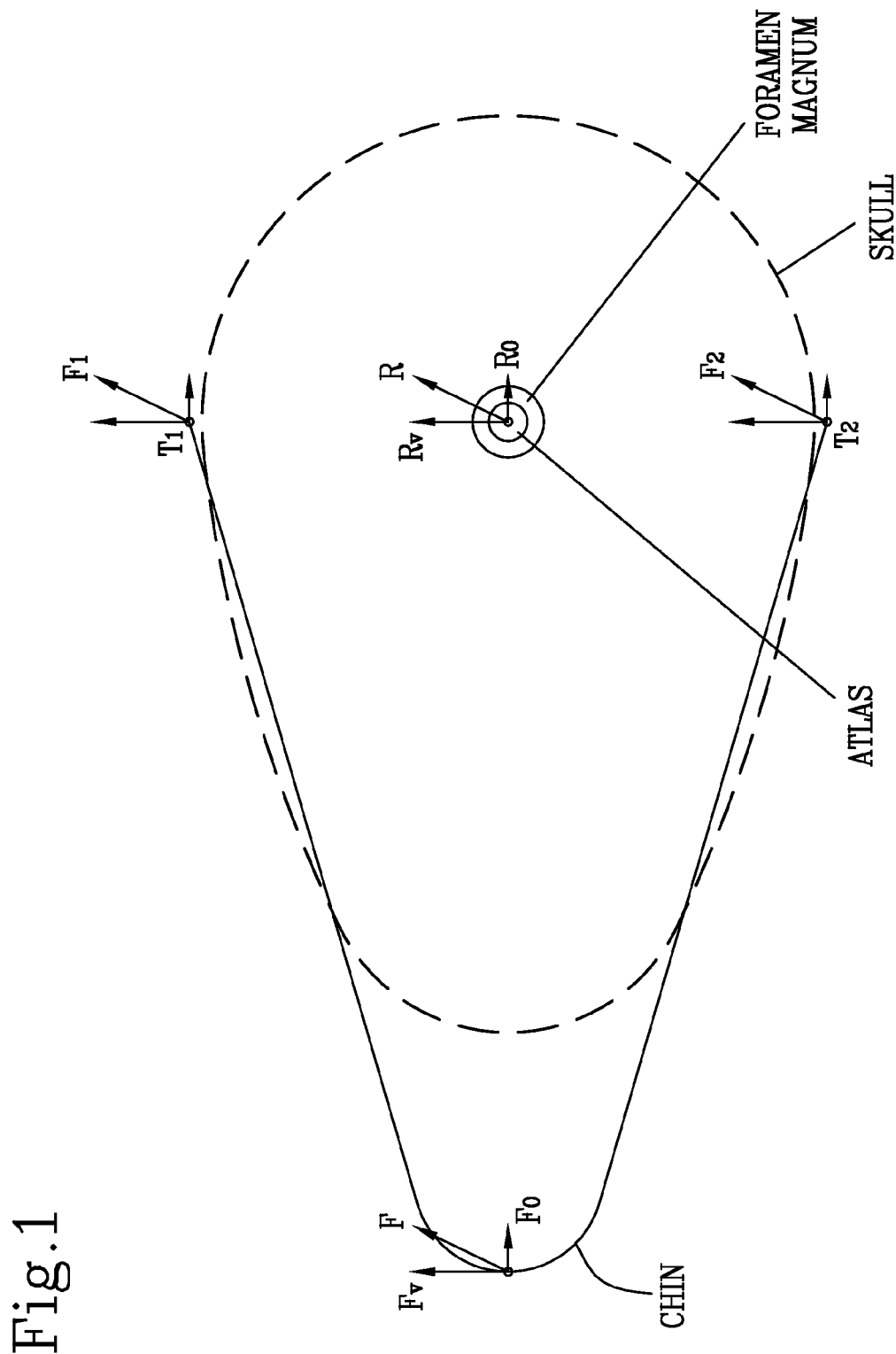
FIG. 1 is a section view of the head, taken on the plane of thrust F, wherein all the forces are represented ovurturned through 90° on the plane of the drawing, where.
Figure 2A:
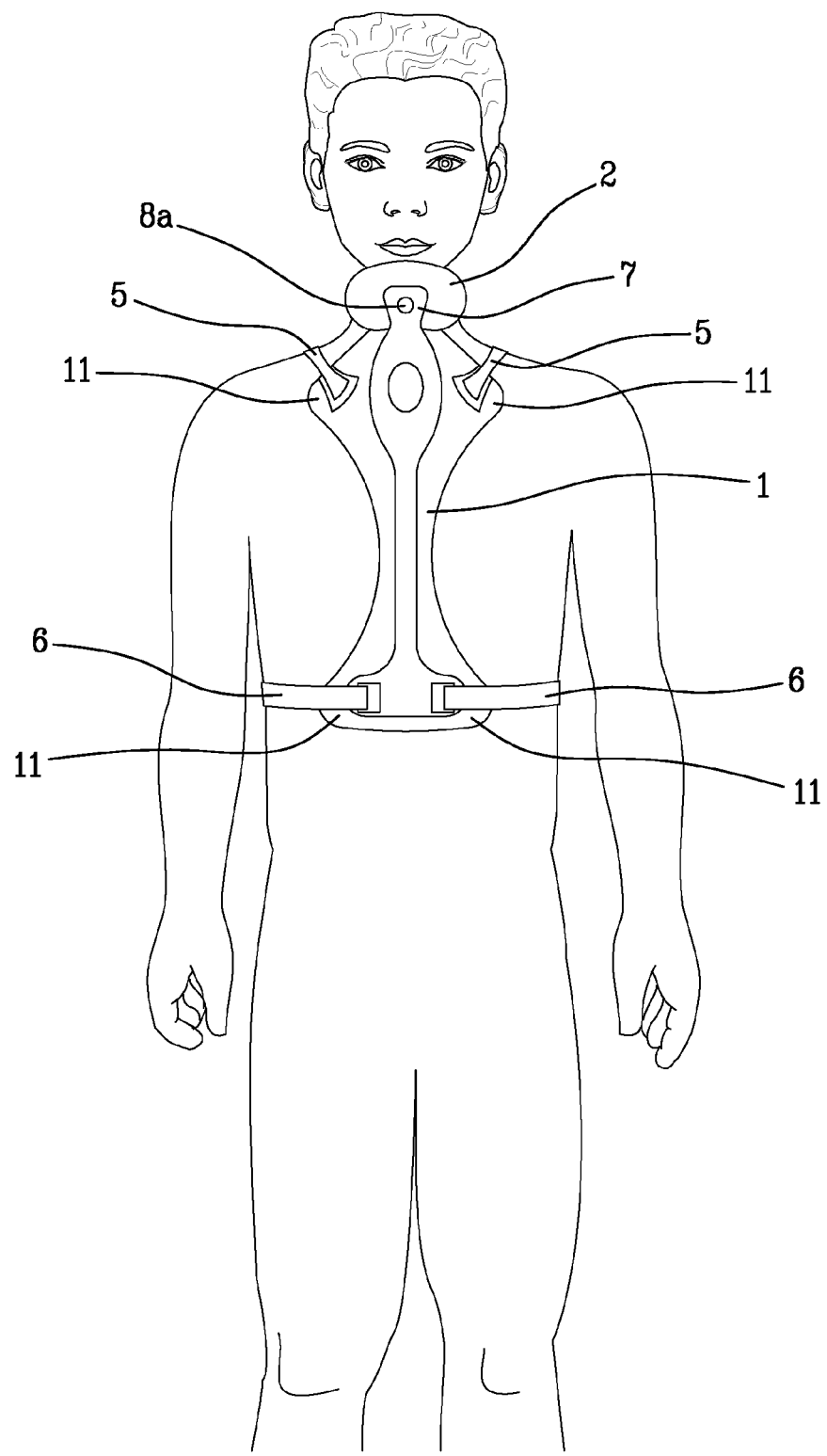

FIG. 2a is an alternative solution of the tutor of FIG. 1.

Figure 3:
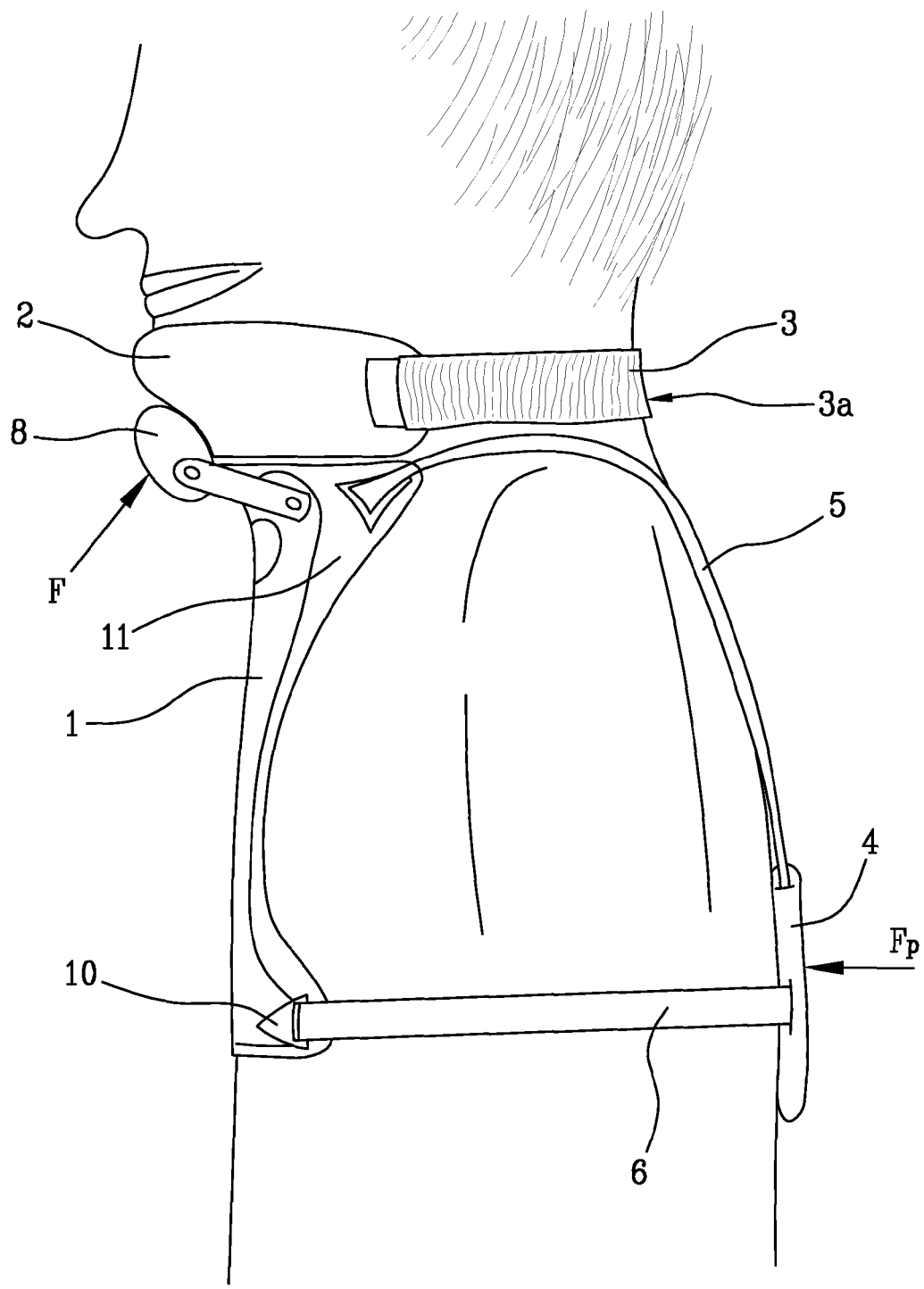

FIG. 3 is a side view of the tutor.

Figure 3A:
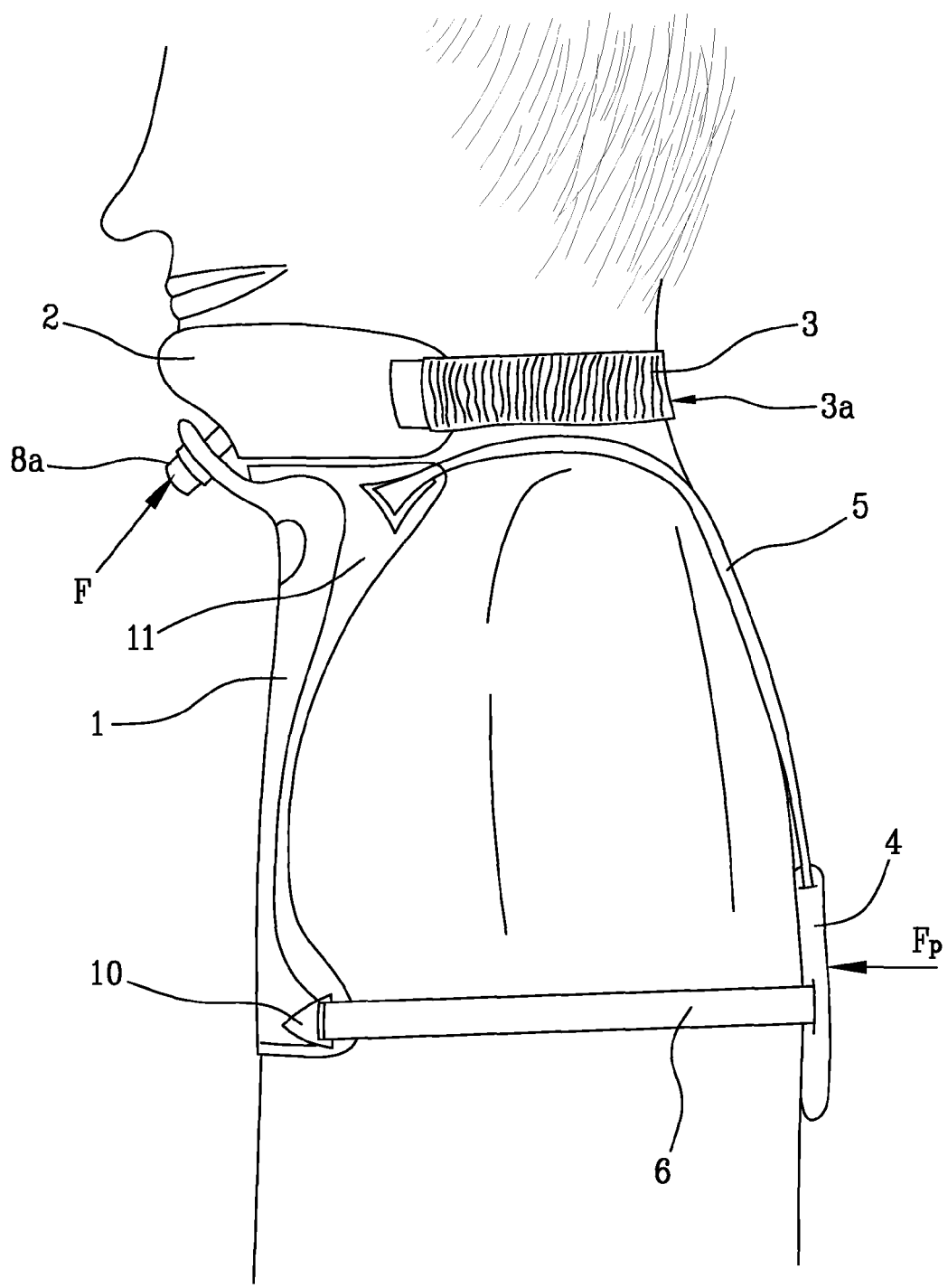

FIG. 3a is an alternative solution of the tutor of FIG. 3.

Figure 4:
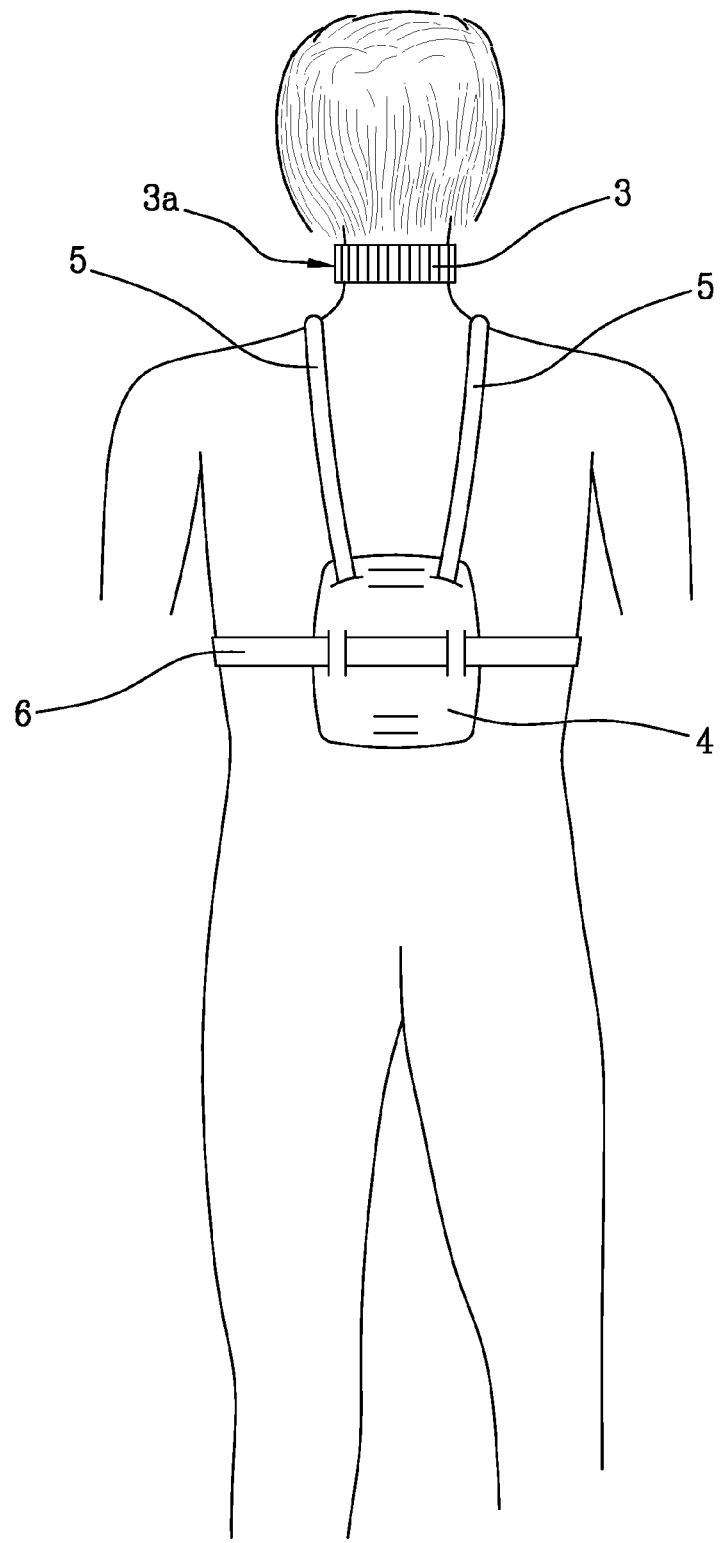

FIG. 4 is a rear side of the tutor.

The invention claimed is:

1. Orthopedic tutor for bloodless correction of the vertebral deformities of a patient, characterized in that it comprises:

a support element (1) to be fixed to the patient's chest and having on top two stretched-apart and symmetrical edges (11);

a chin rest (2) centrally connected to the support element by means (7) capable of causing the vertical oscillation thereof and also laterally connected to an anchoring means (3) for accommodating the chin of the patient having closed mouth and head forward inclined, and for transmitting an upwardly directed anteroposterior thrust (F) to the patient's yaw, means (8a) made up of a screw-and-nut element articulated to said support element (1) and located in front of the chin rest (2) and oriented perpendicular to the chin rest (2) for generating this thrust (F) on the chin rest (2);

a plate (4) to be positioned in correspondence of the convexity of the patient's dorsal curve and being provided with sustaining means (5) and with tensile means (6) for exerting a posteroanterior force (Fp) applied thereto.

2. Orthopedic tutor according to claim 1, characterized in that it is provided with a retainer element for locking said means (8a) in order to keep constant in time an intensity of the thrust (F) generated by the same means.

3. Orthopedic tutor according to claim 2, characterized in that said means (8a) used to exert the thrust (F) onto the chin rest (2) are operable also by the patient himself/herself.

4. Orthopedic tutor according to claim 3, characterized in that said means (5) consist of two belts passing over the shoulders of the user and able to be fixed on the upper part of the support element (1).

5. Orthopedic tutor according to claim 4, characterized in that said tensile means (6) consist of a belt connected to said plate (4) wound up around the patient's body and fixed to the lower part of support element (1) by means of one or two buckles (7).

6. Orthopedic tutor according to claim 1 characterized in that said support element (1) is made of a rigid material.

7. Orthopedic tutor according to claim 6, characterized in that said means (7) consist of a hinge shaped like a horizontal pivot.

8. Orthopedic tutor according to claim 1 characterized in that said anchoring means (3) is made up of an elastic band (3a).

9. Method for using the orthopedic tutor according to claim 1, characterized in that it comprises:

putting on the tutor with the support (1) laying on a user's chest and fixing it therein by belt(s) (6) anchored to a dorsal plate (4) and wrapped around a body by means of the two belts (5) also anchored to the dorsal plate (4) and passing over the shoulders;

fitting the chin rest (2) by tensioning an anchoring elastic band (3a) at the back of the user's nape;

activating the means (6) intended to exert the desired anteroposterior thrust (F) upwardly oblique with respect to the user's, which force, through the yaw of same user is transmitted also to the first vertebra of the user's cervical curve, thereby generating a retropositioning and an upward stretching and, consequently, a direct straightening of the underlying dorsal curve;

tensioning the belt(s) (6) to obtain the desired posteroanterior thrust acting on the convexity of the user's dorsal curve.

10. Method according to claim 9, characterized in that it determines a reflex action of paravertebral and intercostal muscles which contributes to the correction of various vertebral segments which make up a rachis.

11. Method according to claim 9, characterized in that it involves the concurrent application of a horizontal posteroanterior thrust (Fp) onto the convexity of the dorsal curve.

12. Method according to claim 9, characterized in that it involves the general stabilization of a rachis.

13. Method according to claim 9, characterized in that it allows reducing a necessary application thereof to a partial period of a day.

\* \* \* \* \*